Figure 1:
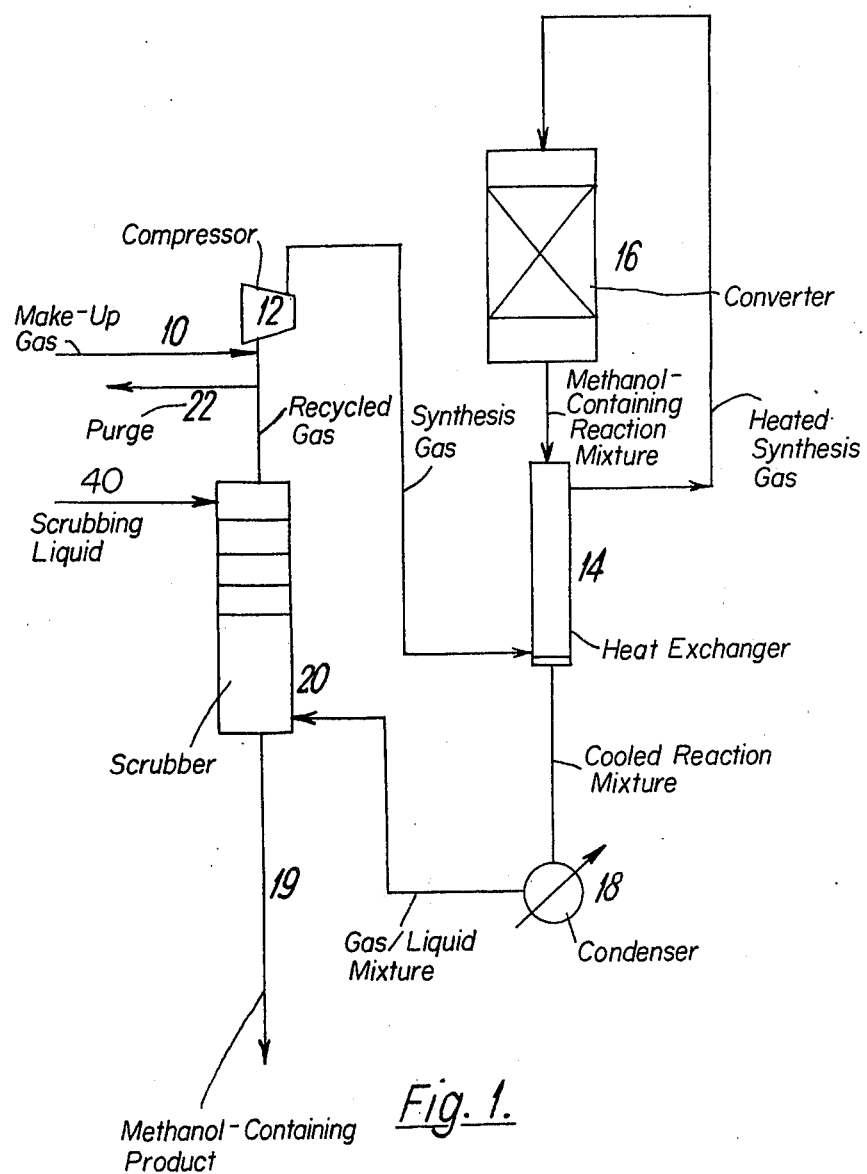

United States Patent [19]
Gent

[11] 3,950,369
[45] Apr. 13, 1976

[54] METHANOL PRODUCTION
[75] Inventor: Alan Edward Alford Gent, Stockton-on-Tees, England
[73] Assignee: Imperial Chemical Industries Limited, London, England
[22] Filed: Mar. 28, 1974
[21] Appl. No.: 455,722

Related U.S. Application Data
[63] Continuation of Ser. No. 215,175, Jan. 3, 1972, abandoned, which is a continuation of Ser. No. 809,777, March 24, 1969, abandoned.

[30] Foreign Application Priority Data
Apr. 8, 1968 United Kingdom............... 16853/68

[52] U.S. Cl. ............................................ 260/449.5
[51] Int. Cl.² ....................................... C07C 29/16
[58] Field of Search ................................. 260/449.5

[56] References Cited
UNITED STATES PATENTS

| | | | |
|---|---|---|---|
| 1,754,371 | 4/1930 | Stengel | 260/449.5 |
| 1,875,714 | 9/1932 | Edmonds | 260/449.5 |
| 2,313,196 | 3/1943 | Guirot | 260/643 D X |
| 2,648,711 | 8/1953 | Carrier | 260/643 D |
| 2,904,575 | 9/1959 | Peet | 260/449.5 |
| 2,964,551 | 12/1960 | Woolcock | 260/449.5 |
| 3,064,029 | 11/1962 | White | 260/449.5 |
| 3,186,145 | 6/1965 | Pelton | 260/449.5 |
| 3,326,956 | 6/1967 | Davies et al. | 260/449.5 |
| 3,501,516 | 3/1970 | Parrish | 260/449.5 |
| 3,531,266 | 9/1970 | Chernoff | 260/449.5 |
| 3,597,465 | 8/1971 | Karofian et al. | 260/449.5 |

FOREIGN PATENTS OR APPLICATIONS

| | | | |
|---|---|---|---|
| 1,489,682 | 6/1967 | France | 260/449.5 |
| 302,297 | 12/1928 | United Kingdom | 55/34 |

OTHER PUBLICATIONS
Petroleum Refiner, Vol. 34, No. 12, pp. 165–167.

Primary Examiner—Howard T. Mars
Attorney, Agent, or Firm—Cushman, Darby & Cushman

[57] ABSTRACT

In a methanol production process synthesis gas containing carbon dioxide is passed over a methanol synthesis catalyst, cooled to remove part of the methanol and water contained in the gas, scrubbed with a liquid to remove substantially the remainder of the methanol contained in the gas, then recycled to the methanol synthesis catalyst. The process affords an economically significant increase in the rate of methanol recovery, especially when the synthesis is operated at low pressures in warm climates.

5 Claims, 2 Drawing Figures

METHANOL PRODUCTION

This is a continuation of application Ser. No. 215,175, filed Jan. 3, 1972, and now abandoned, which in turn is a continuation of Ser. No. 809,777, filed Mar. 24, 1969, now abandoned.

This invention relates to a process of producing methanol and in particular to an improvement in the recovery of methanol from a gas stream containing it.

Our prior U.S. Pat. No. 3,326,956 and in our said co-pending British application No. 35368-41002/65 corresponding to U.S. application Ser. No. 570,687 filed Aug. 8, 1966, describe methanol production processes in which the synthesis of methanol involves passing a synthesis gas containing carbon monoxide and carbon dioxide and hydrogen over a copper-containing catalyst at pressures below 150 atmospheres. Processes at such pressures inevitably are subject to the thermodynamic limitations, as compared with earlier processes at higher pressures, that the conversion to methanol in each pass of the synthesis gas through the catalyst is not very high and that the efficiency with which methanol can be condensed out of the gas tends to be rather low unless cooling water is available at a low temperature or special cooling arrangements are adopted. Thus design problems are encountered when such processes are to be operated in warm climates.

We have now realised that conditions encountered in such processes can be exploited to make possible a simple procedure for increasing the efficiency of recovery of methanol.

According to the invention there is provided a methanol production process in which synthesis gas containing carbon dioxide is passed over a methanol synthesis catalyst, cooled to remove part of the methanol and water contained in the gas, scrubbed with a liquid to remove substantially the remainder of the methanol in the gas, then recycled to the methanol synthesis catalyst.

Those familiar with synthesis processes will understand that the process of the invention includes in practice also the addition of further synthesis gas ("make-up-gas") to the synthesis recycle system at some stage, usually after the methanol removal operations, and that the recycled gas or make-up gas or both must also contain hydrogen and will usually contain carbon monoxide. Usually also some gases inert in the methanol synthesis are present, such as methane, and possibly also nitrogen or argon. Consequently the synthesis recycle loop usually includes provision for limiting the inerts concentration by purging and may be operated in combination with means to produce further carbon oxides and hydrogen from methane in the purge gas, for example as described in our co-pending British application No. 3065/67.

In the process of the invention the methanol synthesis stage is typically at a pressure below 150 atmospheres, for example 10–150 and especially 30–120, for example 40–80 atmospheres. The temperature is preferably in the range 160°–300°C. Such processes can be conveniently operated using copper-based catalysts, especially those containing copper, zinc and a third component, especially chromium or the oxide of at least one metal from Groups II to IV of the Periodic Table, especially aluminium or magnesium. The process of the invention is especially suitable for the production of methanol in town-gas plants, for example for storage to provide for high-output peak-load gas-making. Such methanol production is usually to be carried out during warm weather and in synthesis systems involving no compression of synthesis gas, so that condensation is necessarily of limited efficiency.

The proportion of carbon dioxide in the synthesis gas should be at least sufficient to afford the higher conversion which is characteristic of the copper-catalysed methanol synthesis using carbon dioxide-containing gas as compared with such a synthesis in which substantially the only carbon oxide is the monoxide. If it is not objectionable to produce a crude methanol containing a substantial proportion of water, for example up to 36% w/w apart from water added in a scrubber, the synthesis gas can contain carbon dioxide but substantially no carbon monoxide. Usually however the percentage by volume of carbon dioxide in the synthesis gas is 1–20, especially 3–12, and is preferably between half and double the carbon monoxide content.

The liquid to be used for scrubbing the synthesis gas after removal of methanol and water by cooling is most conveniently water, since this is already a constituent of the condensate and can either be tolerated if the crude methanol is to be used without purification or can be removed in the distillation plant normally needed for purifying the crude. As an alternative, liquids of lower vapour pressure than water, provided they are tolerable or easily separated, can be used, for example higher alcohols and glycerol. The condensate and the scrubber product can if desired be kept separate and worked up in different ways, for example by feeding them at different levels of a distillation column.

One advantage of the process of the invention is that the scrubbing step can be very simply incorporated into a conventional methanol synthesis system, that is, one including recovery by condensation only. Such systems normally include downstream of the condenser a catch-pot for separating liquid from gas and retaining any liquid droplets and mist. For the process of the invention the catch-pot is preceded by or adapted to include a scrubber providing a short column down which water can be passed. The column is preferably of the tray type.

As a result of the scrubbing step a smaller quantity of methanol is recycled than in processes relying on condensation only. This enables a given methanol output to be obtained from a plant employing substantially smaller vessels, machines and pipework and energy consumption than were previously required. A further economy can be achieved by operating the condensation step at less efficiency than would be needed if no scrubber were used, that is, by using a still smaller condenser and recovering proportionately more methanol by scrubbing; in this form of the invention the gas and liquid leaving the condenser are preferably in the temperature range 35°–50°C for a synthesis process operated at 40–80 atmospheres pressure.

The invention provides as a further feature an apparatus which comprises within a common outer shell means for separating an entrained liquid from a gas and means for scrubbing the gas after it has been subjected to the separating means. Suitably the apparatus comprises a vertical cylinder in the lower portion of which is disposed a gas-liquid separator: this can for example be of the tangential type, or of the impingement type, for example a conical surface at the apex of which the gas-liquid mixture is to be directed. Suitably in the upper portion of such a vessel there is disposed a scrubber section in the form of a set of trays and means for supplying these with a downward flow of scrubbing liquid. Downstream of the scrubber section there should preferably be further gas-liquid separating means, including filter pads and, if desired, separating means of for example the impingement type.

FIG. 1 shows by way of example a flowsheet of the process according to the invention. Compressed make-up gas containing $CO_2$, $CO$, $H_2$ and $CH_4$ enters at 10 from a naphtha/steam reforming plant and after mixing with recycled gas is pumped by circulating compressor 12 to heat interchanger 14 where it is warmed from about 35°C to for example 210°C, at which temperature it enters the catalyst bed in converter 16. After reaction of part of the gas to form methanol, which is an exothermic reaction, the gas leaves the converter at for example 240°C and then is cooled as it gives up part of its sensible heat to the incoming gas in heat interchanger 14. In condenser 18 the gas is cooled to about 35°C by indirect heat exchange with cooling water and the bulk of the methanol and water are condensed. The resulting gas/liquid mixture passes to the catchpot/scrubber 20, in the lower portion of which methanol and water are separated from the gas and in the upper portion of which further methanol is scrubbed from the gas. The product stream of aqueous methanol is taken off at 19. A gaseous purge is taken at 22. The remainder of the gas is recycled by circulating compressor 12.

Figure 2:
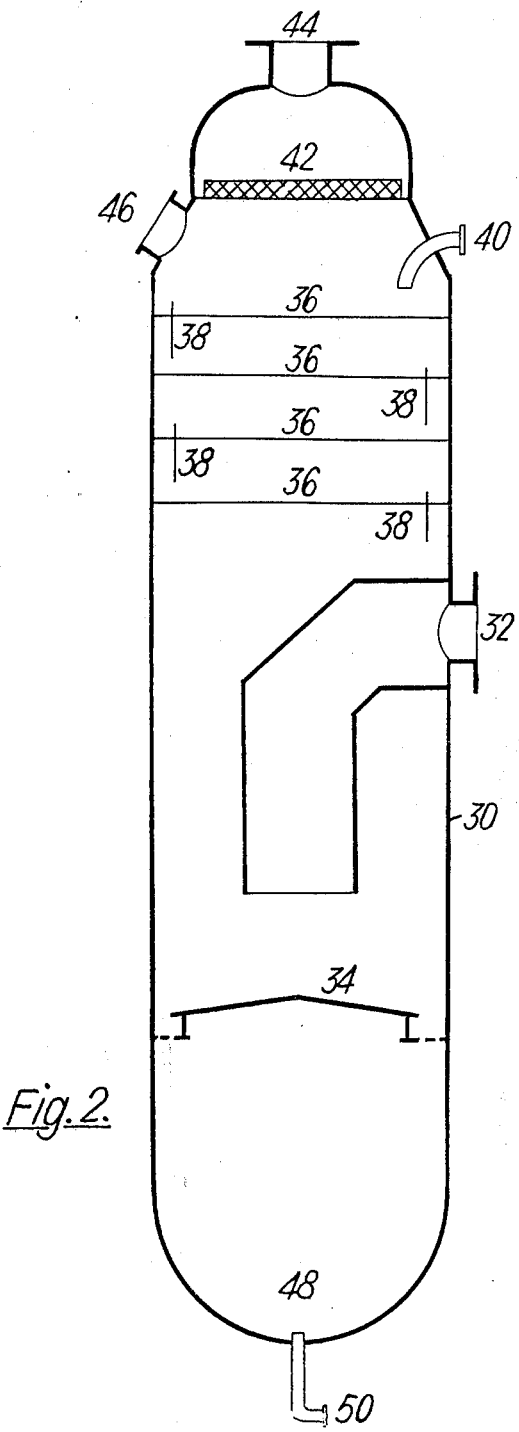

FIG. 2 of the accompanying drawings shows in sectional elevation one preferred form of catchpot-scrubber apparatus according to the invention. This consists of an external shell 30 carrying an inlet port 32 which feeds on to conical impingement surface 34. Above the inlet port are disposed gas-liquid contact plates 36, each including a weir and downcomer 38, of which 4 are shown. Liquid is fed on to the plates by means of feed-pipe 40. Above the gas-liquid contact zone is demisting pad 42 and, at the top of the vessel the gas outlet port 44. Port 46 is for access purposes. Below the impingement surface 34 is a sump 48 and product outlet pipe 50.

In the operation of the apparatus, the incoming gas containing liquid droplets first deposits a substantial proportion of droplets on surface 34, then passes up the downcomers 38 and across the plates 36 in contact with the down-flowing liquid, where further droplets and soluble vapours are absorbed from it. Finally any droplets of absorbent liquid are absorbed in pad 42 and the gas passes out through port 44.

EXAMPLE

A methanol synthesis plant is operated at 50 atmospheres pressure and a catalyst bed outlet temperature of 243°C with a gas having the volume percentage composition $CO_2$ 8.3, $CO$ 8.2, $H_2$ 58.7, $CH_4$ 20.3 at the entry to the catalyst bed, at a total space velocity of 9600 hour$^{-1}$. At the first stage of methanol recovery, using a condenser cooled by water at 30°C, a crude methanol is condensed at 38°C containing 70–80% w/w of methanol and 20–30% w/w of water at the rate of 20 metric tons per hour. The gas/liquid mixture leaving this stage contains 0.54% v/v of methanol vapour and is passed to a catchpot-scrubber at the bottom of which are gas/liquid separation surfaces and at the top of which are nine plates down through which water is passed at the rate of 7 metric tons per hour. (This catchpot-scrubber takes the place of the catchpot containing only the gas/liquid separation surface which would have been used in a process not according to the invention.) From the trays of the scrubber is recovered a solution containing 30% w/w of methanol and 70% w/w of water at the rate of 10 metric tons per hour. The gas leaving the scrubber contains less than 0.1% v/v of methanol vapour. Thus, in comparison with what is possible using the catchpot without a scrubber section, and without allowing for the increased synthesis conversion due to the smaller quantity of recycled methanol, the total output of methanol is increased by 3 metric tons per hour, at an extra cost due to the slightly more expensive scrubber in place of the catchpot and due to the need to distil 10 more metric tons per hour of crude product. It is evident that the invention enables a plant for producing the original output of methanol to be designed with a substantially smaller heat exchanger, converter, cooler, circulating compressor and pipework and thus also energy consumption, than was possible without the scrubber.

I claim:

1. In a process for the production of methanol by passing a gas comprising hydrogen and carbon dioxide over a methanol synthesis catalyst which consists essentially of copper, zinc and a third component which is chromium or a metal oxide from Groups II to IV of the Periodic Table at a pressure below 150 atmospheres and a temperature up to 300°C. to form a gaseous reaction mixture including methanol and water and unreacted carbon dioxide and then recovering the methanol from said gaseous reaction mixture, the improvement whereby the efficiency of the methanol recovery is increased, said improvement comprising the steps of cooling said gaseous reaction mixture to condense part of the methanol and water therein, scrubbing the remaining gaseous mixture with water to remove substantially the remainder of the methanol therefrom and recycling the scrubbed gas for further contact with said methanol synthesis catalyst.

2. A process according to claim 1 in which the pressure is in the range 40–80 atmospheres.

3. A process according to claim 1 in which the methanol synthesis stage is at a temperature in the range 160°–300°C and the reaction mixture is cooled to 35°–50°C before scrubbing.

4. A process according to claim 1 wherein the carbon dioxide gas is used in admixture with carbon monoxide and the proportion of carbon dioxide in the mixture is between half and double that of carbon monoxide.

5. A process according to claim 1 wherein the mixture obtained when the gaseous reaction mixture is cooled to condense methanol and water therein is fed to a separation stage where the uncondensed gas is separated from condensed methanol and water, and the thus separated gas is scrubbed, before it is recycled, the separation of the condensed methanol and water in said separation stage being carried out in the presence of liquid effluent from said scrubbing.

* * * * *